United States Patent
Greenan

(10) Patent No.: US 7,717,950 B2
(45) Date of Patent: May 18, 2010

(54) DOUBLE SHEATH DEPLOYMENT SYSTEM

(75) Inventor: Trevor Greenan, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 899 days.

(21) Appl. No.: 11/202,972

(22) Filed: Aug. 12, 2005

(65) Prior Publication Data
US 2005/0283223 A1   Dec. 22, 2005

Related U.S. Application Data

(62) Division of application No. 10/641,825, filed on Aug. 16, 2003, now Pat. No. 6,945,990.

(51) Int. Cl.
*A61F 2/00* (2006.01)

(52) U.S. Cl. .................. 623/1.12; 623/903

(58) Field of Classification Search ....... 623/1.11–1.54, 623/903; 606/200, 108, 113, 127, 159, 192–198, 606/110; 604/264, 104–107
See application file for complete search history.

(56) References Cited

U.S. PATENT DOCUMENTS

| | | | |
|---|---|---|---|
| 5,683,451 A * | 11/1997 | Lenker et al. | 623/1.11 |
| 5,800,517 A | 9/1998 | Anderson et al. | |
| 5,824,041 A | 10/1998 | Lenker et al. | |
| 5,843,031 A * | 12/1998 | Hermann et al. | 604/95.01 |
| 6,093,203 A * | 7/2000 | Uflacker | 623/1.12 |
| 6,126,685 A | 10/2000 | Lenker et al. | |
| 6,183,481 B1 | 2/2001 | Lee et al. | |
| 6,235,051 B1 | 5/2001 | Murphy | |
| 6,254,609 B1 * | 7/2001 | Vrba et al. | 606/108 |
| 6,315,792 B1 | 11/2001 | Armstrong et al. | |
| 6,350,278 B1 * | 2/2002 | Lenker et al. | 623/1.12 |
| 6,602,280 B2 * | 8/2003 | Chobotov | 623/1.11 |
| 6,723,116 B2 * | 4/2004 | Taheri | 623/1.11 |
| 2002/0099431 A1 | 7/2002 | Armstrong et al. | |
| 2003/0004561 A1 | 1/2003 | Belding et al. | |

* cited by examiner

*Primary Examiner*—Anhtuan T Nguyen
*Assistant Examiner*—Elizabeth Houston
(74) *Attorney, Agent, or Firm*—Teresa Medler

(57) ABSTRACT

A stent-graft deployment system (10) includes a stent-graft (15), a flexible catheter tip (12) attached to a catheter shaft (25), a retractable primary sheath (20) containing the stent-graft in a first constrained small diameter configuration around the catheter shaft near the flexible tip. The stent-graft deployment system further includes a flexible secondary sheath (14) disposed within the retractable primary sheath and also containing the stent-graft, wherein when the primary sheath is removed from around the stent-graft, the flexible secondary sheath contains the stent-graft in a second constrained small diameter configuration around the catheter shaft near the flexible tip. The removal of the secondary sheath releases the stent-graft from a radial constraint so that stent-graft deployment may proceed.

6 Claims, 4 Drawing Sheets

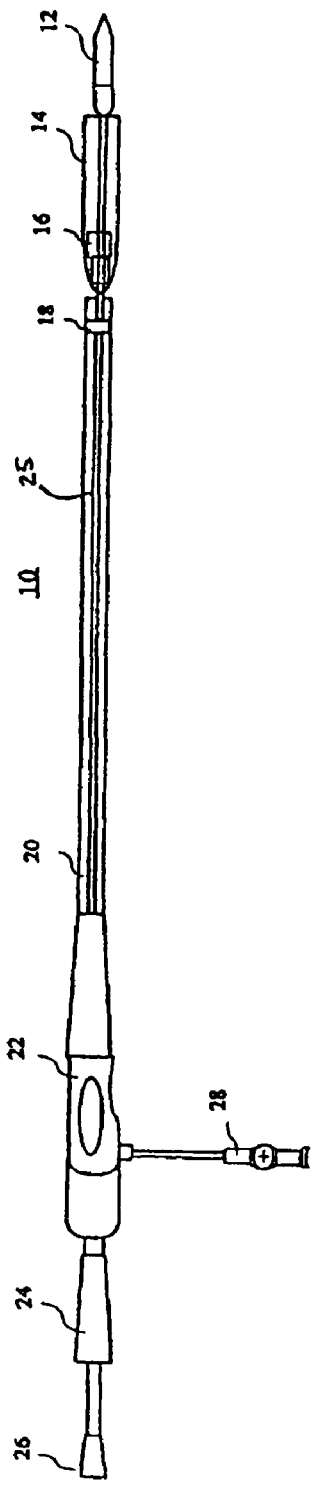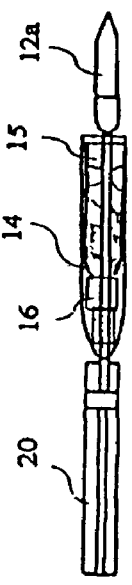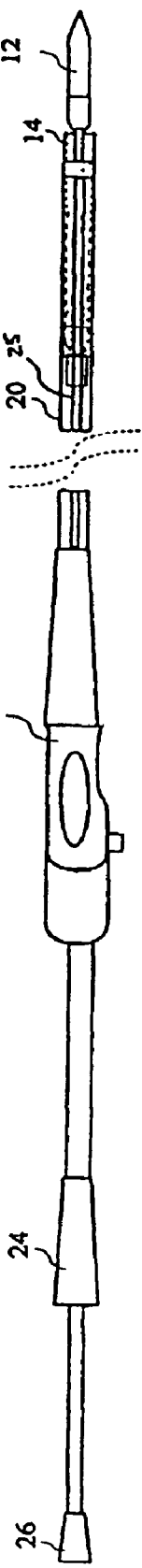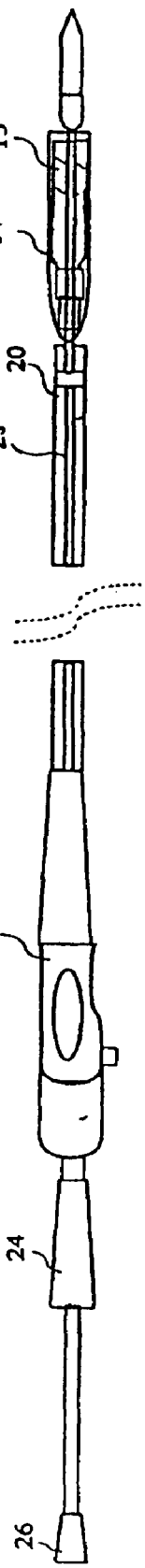
FIG. 1
FIG. 2
FIG. 3
FIG. 4
FIG. 5

DOUBLE SHEATH DEPLOYMENT SYSTEM

This application is a division of U.S. patent application Ser. No. 10/641,825 filed Aug. 16, 2003.

FIELD OF THE INVENTION

This invention relates generally to medical devices and procedures, and more particularly to a method and system of deploying a stent-graft in a vascular system.

BACKGROUND OF THE INVENTION

Prostheses for implantation in blood vessels or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass damaged or occluded natural blood vessels. A graft material supported by framework is known as a stent-graft or endoluminal graft. In general, the use of stent-grafts for treatment or isolation of vascular aneurysms and vessel walls which have been thinned or thickened by disease (endoluminal repair or exclusion) are well known. Many stent-grafts, are "self-expanding", i.e., inserted into the vascular system in a compressed or contracted state, and permitted to expand upon removal of a restraint. Self-expanding stent-grafts typically employ a wire or tube configured (e.g. bent or cut) to provide an outward radial force and employ a suitable elastic material such as stainless steel or Nitinol (nickel-titanium). Nitinol may additionally employ shape memory properties. The self-expanding stent-graft is typically configured in a tubular shape of a slightly greater diameter than the diameter of the blood vessel in which the stent-graft is intended to be used. In general, rather than inserting in a traumatic and invasive manner, stent-grafts are preferably deployed through a less invasive intraluminal delivery, i.e., cutting through the skin to access a lumen or vasculature or percutaneously via successive dilatation, at a convenient (and less traumatic) entry point, and routing the stent-graft through the lumen to the site where the prosthesis is to be deployed.

Intraluminal deployment is typically effected using a delivery catheter with coaxial inner (plunger) and outer (sheath) tubes arranged for relative axial movement. The stent graft is compressed and disposed within the distal end of an outer catheter tube in front of an inner tube. The catheter is then maneuvered, typically routed though a lumen (e.g., vessel), until the end of the catheter (and the stent-graft) is positioned in the vicinity of the intended treatment site. The inner tube is then held stationary while the outer tube of the delivery catheter is withdrawn. The inner tube prevents the stent-graft from being withdrawn with the outer tube. As the outer tube is withdrawn, the stent-graft radially expands so that at least a portion of it is in substantially conforming surface contact with a portion of the interior of the lumen e.g., blood vessel wall.

Most stent-graft deployment systems use only a semi-rigid sheath in the deployment systems. The semi-rigid sheath provides columnar strength to advance the system through access vessels in the body. Unfortunately, the semi-rigid sheath may tend to kink in areas having tight radiuses such as the thoracic arch. Such kinking can increase the deployment force required to place a stent-graft in a target area or even prevent deployment completely. Even if kinking can be avoided, use of a semi-rigid sheath may still increase the pushing force needed to overcome frictional resistance required to deploy the stent-graft to the target area.

One attempt to overcome this problem by W. L. Gore utilized a flexible jacket that deploys the stent-graft with a ripcord that opens the jacket along the longitudinal axis of the flexible jacket, e.g., U.S. Pat. No. 6,315,792. Another single step sheath release initiation is disclosed in U.S. Pat. No. 5,824,041 to Lenker. Unfortunately, these methods introduced a separate non-integrated sheath into the system into the femoral artery and further failed to provide the desired control during deployment. Thus, a need exists for a method and deployment system that avoids kinking (reductions in area or change in shape which creates resistance to deployment) and reduces forces during deployment of stent-grafts in areas having tight radiuses, yet provides appropriate control and in addition provides flexibility during advancement in areas having tight radiuses.

SUMMARY OF THE INVENTION

In one aspect according to the present invention, a stent-graft deployment system comprises a retractable primary sheath, a secondary sheath initially covered by the retractable primary sheath, a stent-graft initially retained within the secondary sheath, and a deployment means for deploying the stent-graft. The secondary sheath is more flexible than the retractable primary sheath. The retractable primary sheath can contain the stent-graft in a first constrained small diameter configuration and the secondary sheath can be disposed within the retractable primary sheath and also contain the stent-graft. When the primary sheath is removed from around the stent-graft, the flexible secondary sheath contains the stent-graft in a second constrained small diameter configuration. The removal of the secondary sheath releases the stent-graft from a radial constraint so that stent-graft deployment may proceed.

In another aspect according to the present invention, a stent-graft deployment system before deployment includes a stent-graft constricted within the flexible secondary sheath, a semi-rigid sheath around the flexible secondary sheath, the semi-rigid sheath being retracted to expose the flexible secondary sheath, and the flexible secondary sheath being retractable such that the stent-graft expands as the flexible secondary sheath is retracted.

In another aspect according to the present invention, a device for implanting a radially self-expanding endoprosthesis comprises an outer sheath which is more rigid and axially maneuverable than an inner sheath. In one configuration the outer sheath is disposed over the inner sheath. While in a second position the outer sheath is retracted to expose the inner sheath. The device further comprises an axially maneuverable elongated catheter coupled to the inner sheath. In a first position the inner sheath retains the radially self-expanding endoprosthesis. As the inner sheath is moved to a second position by for example pulling the proximal end of the inner sheath, the radially self-expanding endoprosthesis is deployed.

A stent-graft deployment system, includes a stent-graft and a catheter having a catheter shaft having a tip; a retractable primary sheath and a retractable flexible secondary sheath. In a predeployed condition the flexible secondary sheath contains the stent-graft in a second constrained small diameter configuration around the catheter shaft at a stent graft location of the catheter near the tip and within the retractable primary sheath. When the primary sheath is retracted from around the stent-graft, the flexible secondary sheath containing the stent graft in the second constrained small diameter configuration is exposed and an end portion of the catheter from an end of the tip to a retracted end of the primary sheath has substantially reduced resistance to bending as compared to when the primary sheath is covering the stent graft location of the catheter. Removal of the secondary sheath releases the stent-graft from a radial constraint so that stent-graft deployment occurs as the secondary sheath releases. Removal of the retractable secondary sheath occurs through a secondary sheath retraction handle connected to a proximal end of the retractable flexible secondary sheath, such that retraction of the secondary sheath retraction handle causes a proximal end of the retractable flexible secondary sheath to be pulled along a catheter longitudinal axis toward a proximal end of the catheter. Pulling of the proximal end of the retractable flexible secondary sheath tensions the retractable flexible sheath to retract the sheath along the catheter longitudinal axis to cause progressive deployment of the stent graft from a distal end of the stent graft.

In another aspect according to the present invention, a method of deploying a stent-graft includes the steps of loading the stent-graft deployment system with a stent-graft, tracking the stent-graft deployment system over a guide wire to a location before a target area which may include a curved portion, and retracting a primary sheath to expose a secondary sheath within said primary sheath while the primary sheath is retracted or held as the secondary sheath is exposed, the stent-graft is moved to its location within the target area or moved until its location within the target area is confirmed. The method further includes the steps of further tracking the stent-graft deployment system to place the secondary sheath in the curved portion of the target area, and retracting the secondary sheath to at least partially deploy the stent-graft in the target area and may include releasing the stent-graft from the delivery system using a release mechanism

BRIEF DESCRIPTION OF THE DRAWINGS

FIG. 1 is a plan view of a stent-graft deployment system without a stent-graft in accordance with the present invention (not to scale);

FIG. 2 is a close up schematic plan view of the end of the deployment system of FIG. 1 having a loaded stent-graft;

FIG. 3 is a close up schematic plan view of the end of the deployment system of FIG. 1 showing an alternative retention mechanism with a loaded stent-graft;

FIG. 4 illustrates the stent-graft deployment system of FIG. 1 with a primary sheath covering a secondary sheath (in dashed lines);

FIG. 5 illustrates the stent-graft deployment system of FIG. 1 with the primary sheath retracted and the secondary sheath exposed;

DETAILED DESCRIPTION

Figure 6:
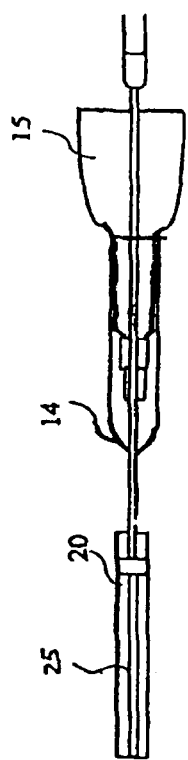
FIG. 6 illustrates the stent-graft deployment system of FIG. 1 with the primary sheath retracted and the secondary sheath partially retracted.

FIGS. 1-3 show portions of a stent-graft deployment system 10. FIG. 1 illustrates the system 10 without a stent-graft while FIGS. 2 and 3 show close up views of the deployment system tip which are loaded with a stent-graft 15, 15a. This system could also deploy a stent alone or some other form of endoprosthesis. The subsequent use of "stent-graft" herein should be understood to include other forms of endoprosthesis. Ideally, the stent-graft deployment system 10 comprises a tapered tip 12, 12a, 12b that is flexible and able to provide trackability in tight and tortuous vessels, and can bend easily once the primary sheath 20 is retracted. Other tip shapes such as bullet-shaped tips could also be used.

The system 10 includes a primary sheath 20 (preferably made of a semi-rigid material such as PTFE) initially covering a secondary sheath 14 (preferably made of woven polyethylene terephthalate (PET)). The secondary sheath 14 is more flexible than the retractable primary sheath 20. The deployment system 10 is able to separately retract the primary and secondary sheaths.

The primary sheath should have enough stiffness to provide adequate trackability and column strength as the system 10 tracks through tortuous vessels to avoid buckling or kinking. The secondary sheath utilizes its greater flexibility (at the expense of column strength) to improve trackability and pushability, particularly through areas having tight radiuses. So, where prior deployment systems utilizing just a semi-rigid primary sheath were prone to kinking while tracking through an area with a tight radius. Use of the secondary sheath avoids kinking or changes in shape and reduces resistance to deployment (reduced advancement force) while tracking through vessels with tight curves.

The deployment system 10 also includes a stent-graft 15 initially retained within the secondary sheath 14. As described herein, the stent-graft 15 is preferably a self-expanding, Nitinol/Dacron stent-graft system designed for endovascular exclusion of Thoracic Aortic Aneurisms (TAA). The deployment system 10 includes a cup 16 as shown in FIG. 2 or alternatively steel runners 17 as shown in FIG. 3 that eventually release the stent-graft by its mere self-expansion to act as a means for retaining the stent-graft 15 in place during deployment. Although the means for retaining shown in FIG. 3 is on the "backend" of the stent-graft, it can alternatively or additionally be on a "tip end" of the stent-graft and attached to one or more of several coaxial tubes. A handle or a hub 22 is fixed to the primary sheath 20, a second handle or hub (24) near a proximal end of the stent-graft deployment system 10 is fixed to the secondary sheath, and a catheter shaft including a shaft handle 26 is connected to and aids the advancement of the system 10 and acts as a deployment means. In addition, the deployment system 10 shown includes a flush port 28 and a radiopaque marker 18 allowing for accurate positioning of the delivery system prior to deployment of the stent-graft in the proximal position.

Figure 10:
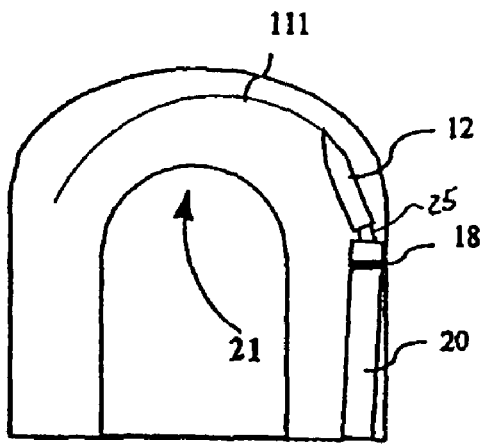
FIG. 10 is a schematic diagram illustrating the stent-graft deployment system initially inserted to a location adjacent (before) a tight curved target area.
Figure 11:
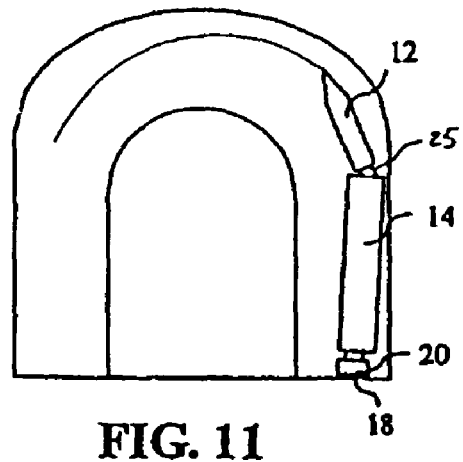
FIG. 11 is a schematic diagram illustrating the stent-graft deployment system showing the primary sheath retracted and the secondary sheath exposed.

Referring to FIGS. 4-8 and FIGS. 10-15, the stent-graft deployment system 10 is shown in various stages as it advances over a guide wire 111 (as shown in FIGS. 10-14) and the stent-graft is deployed. FIGS. 4-8, in particular, illustrate the stent-graft deployment system 10 as it would operate or function outside or apart from the body. FIGS. 10-15 illustrate the stent-graft deployment system as it would operate when tracking over a guide wire 111 within a body and particularly through a target area (vessel) having a tight curvature or radius (21). FIGS. 4 and 10 both illustrate the stent-graft deployment system 10 with the primary sheath 20 covering the secondary sheath 14. The flexible secondary sheath 14 is arranged within the semi-rigid sheath 20 when the semi-rigid sheath 20 is in a non-retracted position as shown in FIG. 4.

As shown in FIG. 5, the stent-graft 15 is constrained solely by the flexible secondary sheath 14 and further illustrates a handle or hub 22 coupled to the semi-rigid sheath 20 serving as a first arrangement for retracting the semi-rigid sheath 20 and exposing the flexible secondary sheath 14 as well as an inner tube 25 coupled to the flexible secondary sheath 14 serving as a second arrangement for retracting the flexible secondary sheath and enabling the stent-graft to expand. It should be noted that the exposed portion of the flexible secondary sheath 14 could have a diameter larger than the semi-rigid primary sheath 20 that surrounded the flexible secondary sheath 14 previously. The larger diameter of the exposed portion of the flexible secondary sheath 14 is a contributory factor in reducing the force needed to retract the secondary sheath. Once the flexible secondary sheath 14 is exposed, the end of stent-graft deployment system 10 beyond the semi-rigid sheath has greater flexibility (than the portion of the system within the semi-rigid sheath 20) as it tracks across the guidewire.

The first arrangement described above could comprise (as previously mentioned) the handle or hub 22 coupled to the semi-rigid sheath 20 enabling the relative axial movement of the semi-rigid sheath 20 over a remainder of the stent-graft deployment system and the second arrangement could comprise an inner tube 25 coupled to the flexible secondary sheath 14 that enables relative axial movement of the flexible secondary sheath 14 relative to the semi-rigid sheath 20 and the longitudinal axis of the catheter. Such as where operation of the second handle 24 causes axial pulling of the proximal end of the flexible secondary sheath 14, to create a tension in the material/fabric of the secondary sheath to cause retraction that causes the cylindrically configured sheath to retract along the longitudinal axis of the catheter to provide a substantially circularly uniform deployment of the stent graft starting at its distal end (relative to the catheter).

Figure 12:
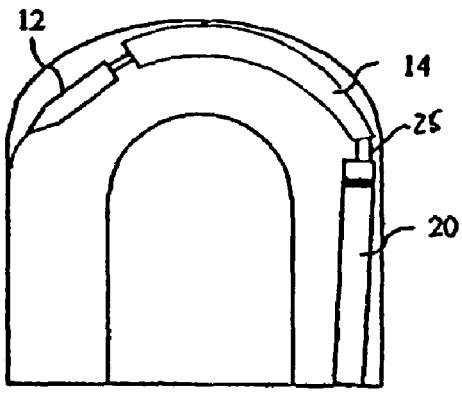
FIG. 12 is a schematic diagram illustrating the stent-graft deployment system with the secondary sheath which is exposed advanced into the tight curve.

In any event, once the secondary sheath 14 is exposed or outside the primary sheath, the system 10 can be advanced over the guide wire 111 with a lower advancement force since the secondary sheath is designed to be quite flexible particularly in areas with tight radiuses (21) as shown in FIG. 12. The tight arch 21 is meant to represent any area or vessels with tight radiuses such as the thoracic arch.

Figure 13:
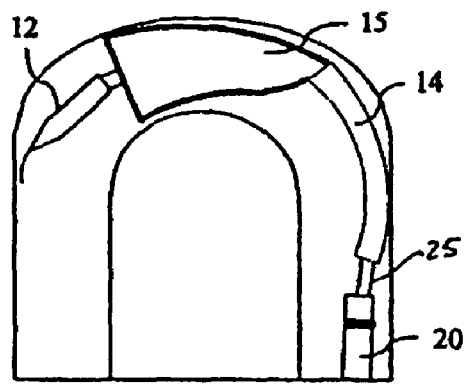
FIG. 13 is a schematic diagram illustrating the stent-graft deployment system with the secondary sheath which has been advanced into the curve is partially retracted and the stent-graft is partially deployed.

Referring to FIGS. 6 and 13, in each instance the primary sheath has been retracted and the secondary sheath is shown partially retracted with the stent-graft 15 being partially deployed. As the secondary sheath retracts, more and more of the stent-graft is deployed as shown in FIGS. 6-8 and FIGS. 13-15.

Figure 8:
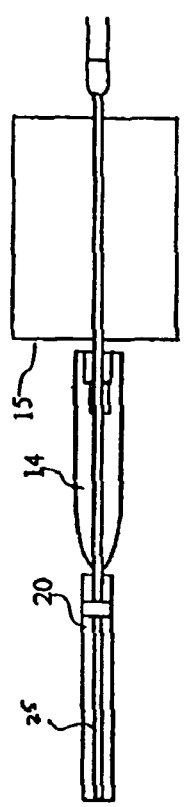
FIG. 8 illustrates the stent-graft deployment system of FIG. 1 with the secondary sheath completely retracted and the stent-graft fully deployed.
Figure 14:
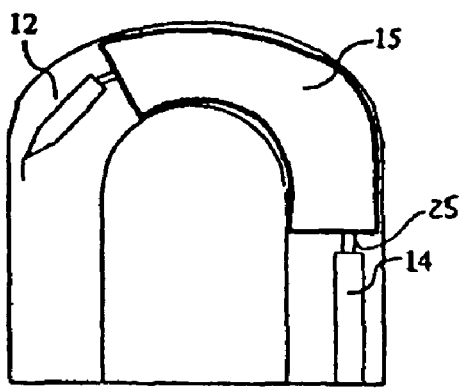
FIG. 14 is a schematic diagram illustrating the stent-graft deployment system with the secondary sheath being completely retracted and a stent-graft being fully deployed.
Figure 15:
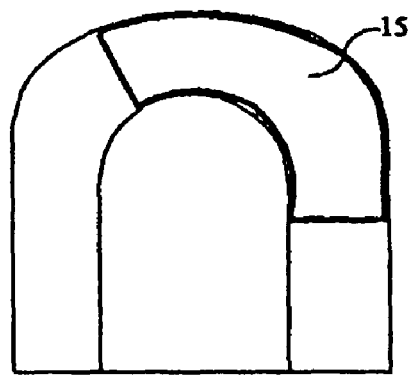
FIG. 15 is a schematic diagram illustrating the stent-graft fully deployed with the stent-graft deployment system removed in accordance with the present invention.

FIGS. 8 and 14 illustrate the stent-graft deployment system 10 with the secondary sheath 14 completely retracted and the stent-graft 15 fully deployed. In FIG. 15 the stent-graft deployment system 10 has been removed.

Figure 7:
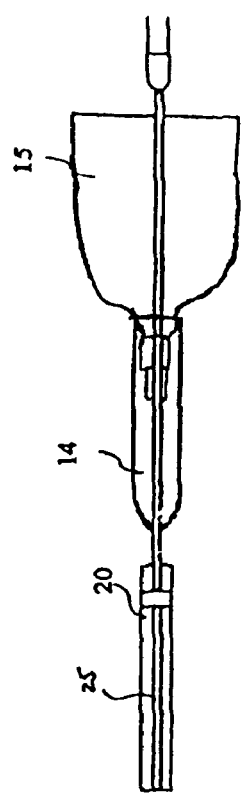
FIG. 7 illustrates the stent-graft deployment system of FIG. 1 with the primary sheath retracted with the secondary sheath almost completely retracted.

The stent-graft deployment system 10 can also be thought of as a device for implanting a radially self-expanding endoprosthesis 15 having an outer sheath 20. As previously explained, the outer sheath 20 is more rigid and axially maneuverable relative to an inner sheath 14 and wherein the outer sheath 20 is disposed over the inner sheath 14 in a first position (as shown in FIG. 5) and exposes the inner sheath 14 in a second position (as shown in FIGS. 6-8). The system 10 can also include an elongated catheter 25 coupled to the inner sheath 14, wherein the inner sheath 14 is constructed to retain the radially self-expanding endoprosthesis 15 in a first position and enable deployment of the radially self-expanding endoprosthesis 15 in a second position.

Figure 9:
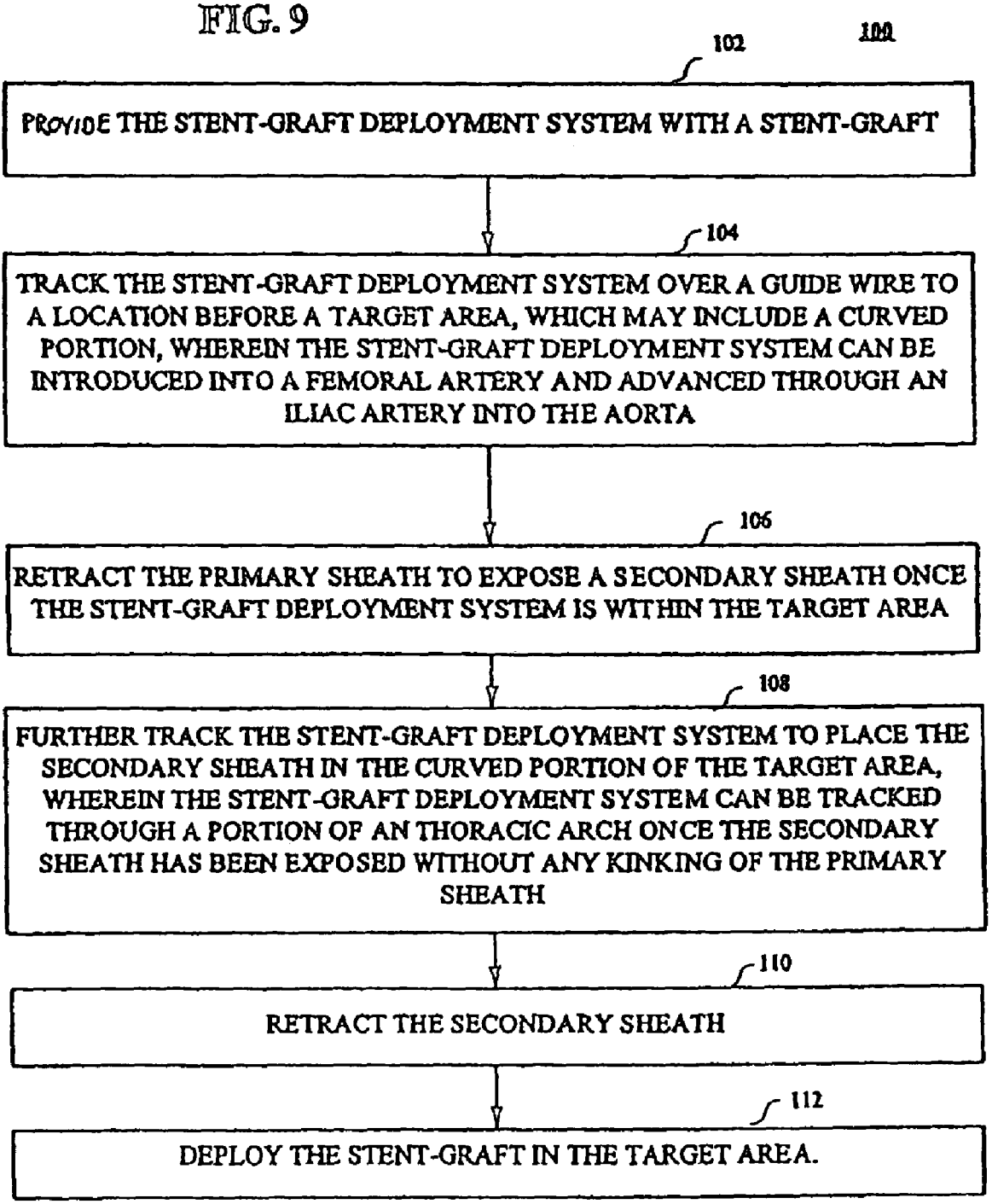
FIG. 9 is a flow chart illustrating the steps of a method in accordance with the present invention.

Referring to FIG. 9, a flow chart illustrates a method 100 of deploying a stent-graft includes the steps of providing a stent-graft deployment system with a stent-graft 102, tracking the stent-graft deployment system over a guide wire to a location before a target area 104, which may include a curved portion, and retracting the primary sheath to expose a secondary sheath within the target area while the primary sheath is retracted or held as the secondary sheath is exposed 106. The stent-graft is moved to its location within the target area or until its location within the target area is confirmed. It should be noted that once the primary sheath is retracted and the secondary sheath is exposed, the secondary sheath (being of a relatively more flexible material than the primary sheath) will provide greater flexibility in tracking through the remainder of the target area regardless of the curvature or tortuous nature of the vessel. The method further includes the steps of further tracking the stent-graft deployment system to place the secondary sheath in the curved portion of the target area 108, and retracting the secondary sheath to at least partially deploy the stent-graft in the target area 110. This step may include deploying or releasing the stent-graft from the delivery system using a release mechanism 112.

The device may also be considered to have a first predeployment configuration wherein said first and second sheaths surround the stent graft to be deployed, and a second partial deployment configuration where the primary sheath is fully retract so that the primary sheath no longer constrains the stent graft to be deployed, while the secondary sheath still constrains the stent graft to be deployed, and third fully deployed configuration where said stent graft is fully released from the primary and secondary sheaths. Wherein the relative movement of the tubular (substantially cylindrical sheaths) is such that the axial centerline of the cylinder forming the sheaths is moved without the sheaths being everted between their respective predeployment configurations and their respective post deployment configurations such that the axial centerline of the cylinder of each sheath moves in substantially one motion (in a linear movement along a curving path) along the axial centerline of the catheter along which it is moved The present configuration is well suited for introducing the stent-graft deployment system into a femoral artery and advancing the stent-graft deployment system through an iliac artery into the aorta for repair of an aortic aneurysm and more specifically in tracking the stent-graft deployment system through a portion of an thoracic arch when the secondary sheath has been exposed after the retraction of the primary sheath and without any kinking of the primary sheath.

Additionally, the description above is intended by way of example only and is not intended to limit the spirit and scope of the invention and it equivalent as understood by persons skilled in the art.

What is claimed is:

1. A method of deploying a stent-graft using a stent-graft deployment system having a retractable primary sheath and a flexible secondary sheath wherein the primary sheath is disposed about the secondary sheath, comprises the steps of:

providing the stent-graft deployment system with a stent-graft, wherein in a predeployed condition said stent-graft is contained within the flexible secondary sheath and retained in a first constrained small diameter configuration by the primary sheath;

tracking the stent-graft deployment system over a guide wire to a location before a target area, wherein the target area may include a curved portion;

retracting the primary sheath to expose the flexible secondary sheath containing the stent graft, wherein when said primary sheath is retracted from around said flexible secondary sheath substantially an entire length of said stent-graft expands within said flexible secondary sheath to a second constrained small diameter configuration larger than said first constrained small diameter;

further tracking the stent graft deployment system to place the secondary sheath containing the stent-graft in the second constrained small diameter configuration to a location within the target area; and retracting the secondary sheath to at least partially deploy the stent-graft in the target area.

2. The method of claim 1, wherein retracting the secondary sheath occurs by pulling a proximal end of said secondary sheath.

3. The method of claim 1, wherein the method further comprises the step of introducing the stent-graft deployment system into a femoral artery and advancing the stent-graft deployment system through an iliac artery into the aorta.

4. The method of claim 1, wherein the step of advancing the secondary sheath containing the stent-graft comprises the step of tracking the secondary sheath containing the stent-graft through a portion of a thoracic arch.

5. The method of claim 1, wherein the steps of tracking and advancing are achieved without kinking of the primary sheath.

6. The method of claim 1 further comprising the step of releasing the stent-graft from the stent-graft deployment system using a release mechanism, which pulls the proximal end of the secondary sheath.

* * * * *